(12) United States Patent
Fuertes et al.

(10) Patent No.: US 8,609,872 B2
(45) Date of Patent: Dec. 17, 2013

(54) METHOD FOR PREPARING DIAHYDROHEXITOL DIESTER COMPOSITIONS

(75) Inventors: Patrick Fuertes, Lomme (FR); Hervé Wyart, Cuinchy (FR)

(73) Assignee: Roquette Freres, Lestrem (FR)

( * ) Notice: Subject to any disclaimer, the term of this patent is extended or adjusted under 35 U.S.C. 154(b) by 170 days.

(21) Appl. No.: 13/348,921

(22) Filed: Jan. 12, 2012

(65) Prior Publication Data

US 2012/0116101 A1    May 10, 2012

Related U.S. Application Data

(62) Division of application No. 11/887,625, filed as application No. PCT/FR2006/000632 on Mar. 22, 2006, now Pat. No. 8,129,549.

(30) Foreign Application Priority Data

Apr. 1, 2005    (FR) ...................................... 05 03241

(51) Int. Cl.
*C07D 493/04*    (2006.01)
(52) U.S. Cl.
USPC ......................................................... 549/464

(58) Field of Classification Search
USPC ......................................................... 549/464
See application file for complete search history.

(56) References Cited

U.S. PATENT DOCUMENTS

| 2,322,821 | A | 6/1943 | Brown |
| 4,297,290 | A | 10/1981 | Stockburger |
| 6,369,140 | B1 | 4/2002 | Staniek |

FOREIGN PATENT DOCUMENTS

| EP | 0 065 267 A | 11/1982 |
| WO | 99/45060 A | 9/1999 |
| WO | 01/83488 A | 11/2001 |

*Primary Examiner* — Bernard Dentz
(74) *Attorney, Agent, or Firm* — Young & Thompson

(57) ABSTRACT

A dianhydrohexitol diester composition is obtained by esterifying a dianhydrohexitol composition with a carboxylic acid in the presence of an acid catalyst and hypophosphorous acid. Preferably, the hypophosphorous acid is introduced in an amount between 0.05 and 2 wt. percent of dianhydrohexitol, and in a hypophosphorous acid/acid catalyst weight ratio of less than 1/1. Dianhydrohexitol diester compositions, for example isosorbide diesters, isomannide and/or isoidide rich in diester(s), and having a low yellow index (YI), are useful in numerous industrial applications, in particular in plastic compositions.

17 Claims, No Drawings

METHOD FOR PREPARING DIAHYDROHEXITOL DIESTER COMPOSITIONS

CROSS REFERENCE TO RELATED APPLICATIONS

This application is a division of copending application Ser. No. 11/887,625 filed on Oct. 15, 2007; which is the 35 U.S.C. 371 national stage of International application PCT/FR06/000632 filed on Mar. 22, 2006; which claims priority to French application 0503241 filed on Apr. 1, 2005. The entire contents of each of the above-identified applications are hereby incorporated by reference.

The subject of the present invention is a novel method for preparing diester compositions of dianhydrohexitols such as isosorbide, isoidide, isomannide or isogalactide.

It also relates, as novel industrial products, to some of these compositions, chosen especially for their characteristics of content of diester(s) and/or coloration.

Finally, it also relates to the use of the aforementioned compositions in various industrial fields, in particular in plastics.

The preparation of esters of anhydrohexitols has been known for more than 60 years and has especially been described in the patents mentioned below, published in the 1940s in the name of Atlas Powder Company:

U.S. Pat. No. 2,322,820 relating to the preparation of compositions of monoesters of hexitans (sorbitan, mannitan) and/or of hexides (sorbide=isosorbide or mannide=isomannide);

U.S. Pat. No. 2,322,821 relating to the preparation of compositions of isosorbide or isomannide monoesters, said compositions possibly containing significant levels of hexide diesters; and U.S. Pat. No. 2,387,842 relating to the preparation of diesters or mixed diesters of isosorbide or isomannide.

In the latter patent, the preparation of diesters is exemplified starting from either a hexitol (sorbitol, mannitol) or from dianhydrohexitol (isosorbide or isomannide). The possibility of starting from a monoanhydrohexitol (or hexitan) is also mentioned without being exemplified.

In any case, whether starting from hexitol or from dianhydrohexitol, the esterification reaction itself is carried out systematically in the presence of toluene as a means for removing water and, in almost all of the examples, in the presence of an acid catalyst, the latter always being concentrated sulfuric acid.

After neutralizing and rinsing with water, the reaction medium undergoes only one treatment of evaporation of toluene under vacuum.

The esters obtained are then tested as plasticizers for plastics (polyvinyl chloride, chloroacetate and butyrol).

At the same time, Patent GB 613,444 mentions the preparation, from isosorbide, of isosorbide ditetrahydrofurcate or dibutyrate with continuous removal of water by reflux then simple distillation under vacuum of the reaction medium.

The isosorbide esters are presented as good softening agents or plasticizers for resins and cellulosic materials.

In 1953, Y. HACHIHAMA and I. HAYASHI (Techno. Repts. Osaka Univ. 1953, vol. 3, pp. 191-200) confirm the advantage of isosorbide diesters as plasticizers for polyvinyl chloride (PVC). The esterification is carried out in the presence of sulfuric acid or para-toluenesulfonic acid (PTSA) and, in almost all of the examples, in the presence of toluene or xylene. No mention is made of any additional means of treatment, in particular of purification.

U.S. Pat. No. 3,023,223 describes the preparation of isoidide (1,4-3,6-dianhydro-L-iditol) by simply stating that it may be converted to diesters that can be used as plasticizers for synthetic resins by esterification with monocarboxylic acids.

U.S. Pat. No. 3,454,603 describes the preparation of isoidide and isosorbide by specifying that by esterification with fatty acids or esters, they may be converted to surfactants.

By way of illustration, reference is only made to the potential preparation of isoidide or isosorbide monostearates in the presence of 0.05% of PTSA at 200° C. for 4 hours in an inert atmosphere. Patent JP 44-2964 describes the preparation of surfactants based on esters of monoanhydrohexitols, in this case sorbitan esters of the "SPAN" type. The authors state that in order to obtain a lower final coloration of said esters, it is advisable to use a catalyst system that compulsorily combines, and in very precise proportions, an alkaline agent (for example sodium carbonate) and either phosphoric acid, or hypophosphorous acid or salts thereof. It appears that the phosphoric acid makes it possible, under these conditions, to achieve a less pronounced coloration than that obtained by hypophosphorous acid. However, this coloration does not appear acceptable and imposes the use of an additional treatment of decoloration by sodium chloride or hydrogen peroxide.

Patent EP 65 267 confirms the use of alkaline catalysts in the preparation of esters of monoanhydrohexitols and the necessity of carrying out a bleaching treatment with hydrogen peroxide ($H_2O_2$) in order to obtain products having a correct coloration.

At the same time, U.S. Pat. No. 4,297,290 published in 1981 describes the manufacture of sorbitan esters according to which the esterification reaction is carried out in the presence of a base and at a temperature that does not exceed 215° C. with a view to obtaining products having improved coloration.

According to the examples of this patent, the esterification is carried out however in the presence of activated carbon as a decolorizing means.

Moreover, the reaction medium is a) neutralized by phosphoric acid with a view to limiting the coloration thereof during a stability test at 93° C. then b) treated with hydrogen peroxide and, each time, filtered in the presence of diatomaceous earth.

Much more recently, Patent Application WO 99/45060 exemplifies, without really explaining it in detail, the preparation of particular diesters of isosorbide or isomannide with a view to their use as solvents or plasticizers for polymers.

This preparation is carried out starting from dianhydrohexitols, in the presence of 4% PTSA and a solvent (xylene). The cooled reaction crude is treated with another solvent (diethyl ether) then rinsed with (NAOH-containing) water and evaporated. According to the examples, the yields of diesters range from 86 to 95%. However, no detail is given or can be deduced as regards the exact conditions, especially temperature, in which the reaction medium is heated/boiled and, especially, evaporated, these conditions inevitably acting on the coloration of the final product.

Lastly, Patent Application WO 01/83488 describes an improved method for preparing sorbitan or isosorbide esters by use of an acid catalyst of the macroporous acid ion-exchange resin type. According to the authors, this use must make it possible to obtain, with high degrees of conversion (98%-100%), products that have a substantially improved color, including with respect to the products disclosed in the aforementioned Application WO 99/45060, and therefore make it possible to be free from any distillation step.

This improvement in color is presented as resulting from the possibility of carrying out, due to said macroporous resins, an esterification reaction at a temperature below 150° C.

Furthermore, the authors emphasize the possibility of obtaining the same effects by starting not from isosorbide but from sorbitol or sorbitan since the dehydration reaction is carried out at a relatively low temperature (120-125° C.) before increasing this temperature to 145-150° C. for the esterification itself.

In any case, this method has the disadvantage of being expensive due to the very fact of the use of said macroporous resins. This is because, besides their high cost, these catalysts are used in significant amounts, namely of around 13% (by dry weight/dry weight of isosorbide) according to the examples of this patent.

The majority of said examples furthermore show:
1. the ever present necessity of distilling the reaction medium for the purpose of removing the excess fatty acid (n-octanoic or 2-ethylhexanoic acids);
2. the necessity of removing the macroporous resin and this, by filtration of the reaction medium previously cooled to 60-80° C.; and
3. the necessity of then treating said reaction medium with activated carbon after having, however, reheated said medium to a temperature of 80-100° C.

Independently of the exact amount of activated carbon used after removal of the macroporous resin, said quantity not being specified in this Application WO 01/83488, it can be admitted that the method thus envisaged is complex in practice as it imposes two filtration steps, one to remove the macroporous resin, the second to remove the activated carbon.

The fact remains nonetheless that this method does not make it possible to obtain a reaction medium, treated over activated carbon, evaporated or not evaporated, which is truly colorless.

At best, the color of this medium is qualified as "pale yellow", without moreover the lowest coloration value being indicated as a function of any measurement technique which would have been itself described.

Example 5 from this patent describes the final production of an isosorbide 2,5-di(n-octanoate) composition, apparently less colored, as it is qualified as "virtually water-white" without any coloration measurement having been carried out.

In any case, the method described specifically in this Example 5 is complicated and expensive as it envisages:
a) the use of activated carbon in two places and in significant amounts, namely 1) an amount of 7% by weight of dry matter/isosorbide dry matter during the esterification reaction then again 2) in an amount of 3.5% by weight of dry matter/isosorbide dry matter after distillation;
b) a double treatment, after distillation of the resulting reaction medium, with 1) an organic solvent, in this case n-hexane, then 2) with activated carbon (cf. supra).

This method is all the more complicated and expensive as the macroporous resin used concomitantly with the activated carbon during the esterification reaction cannot be effectively reused as it is polluted by said carbon and by the coloring species absorbed by this.

Specifically regarding the preparation of dianhydrohexitol diesters, it appears that despite the means available to a person skilled in the art, capable of helping the purification and/or the decoloration of these products and more widely anhydrohexitol esters, it has not been possible to date to have an industrial process which is at the same time simple, economic, high-performance and without danger, and in particular a process which, simultaneously:

a) does not impose the compulsory use of macroporous resins during the esterification reaction but can also be applied to conventional, less expensive catalysts such as, for example, sulfuric acid or PTSA;
b) makes it possible to obtain high contents of dianhydrohexitol diesters, namely contents greater than 90%, preferably at least equal to 95% and more preferably still at least equal to 98% and this, without compulsorily using a purification means other than a conventional distillation treatment and in particular without use of the slightest organic solvent;
c) does not impose the compulsory use of several steps of treatment with activated carbon and/or significant amounts (namely greater than 3-4%, in particular at least equal to 5%, expressed by weight of dry matter relative to the dry weight of starting dianhydrohexitol) of activated carbon for the purpose of obtaining products with acceptable color;
d) does not impose the compulsory use of hydrogen peroxide with a view to obtaining products of acceptable color;
e) makes it possible to further improve the color of intermediate or final compositions of such diesters and this, without upsetting the general economy of the method; and
f) can advantageously be applied not only to the preparation of isosorbide or isomannide diesters, a preparation relatively documented in the prior art, but also to that of diesters of other dianhydrohexitols and in particular to the preparation, never truly exemplified hitherto, of isoidide diesters.

The merit of the Applicant is to have found, after much research and analysis, that such a means consisted of a method having the double characteristic:
1. of compulsorily starting from dianhydrohexitol, and not from hexitol or hexitan (monoanhydrohexitol), as raw material; and
2. compulsorily using, during esterification, a) an acid catalyst and b) hypophosphorous acid.

The Applicant has initially observed during a first series of studies, that it was not possible, starting from hexitol (for example sorbitol) to prepare a composition having a content of dianhydrohexitol diester (for example isosorbide di(n-octanoate)) exceeding or even reaching the value of 85%. Among the very many acid catalysts tested, the macroporous resins were shown, on this occasion, to be the most effective without however making it possible to obtain a diester content greater than about 78-81%. A conventional catalyst such as PTSA has not made it possible here to achieve a diester content of 70% and this, even by varying the operating conditions (PTSA/sorbitol ratio, conditions of use of n-octanoic acid, reaction temperatures, etc.). This is because, starting from hexitol as raw material, it has been observed in all cases, including in the presence of macroporous resin as a catalyst, a very large co-production of species other than the desired diester(s), in particular monoanhydrohexitol triesters and tetraesters (for example sorbitan trioctanoates and tetraoctanoates).

This is why, during a second series of studies, the Applicant resolutely decided to use a dianhydrohexitol (for example, isosorbide) as raw material with a view to preparing any desired diester (for example isosorbide dioctanoate).

On this occasion, it was observed that not only was it possible to obtain compositions rich in diester(s) without compulsorily using a macroporous resin but using any type of acid catalyst for esterification, but also that the additional use of hypophosphorous acid, during the esterification reaction, made it possible to obtain specific and particularly advantageous effects in terms of absence of color of the diester composition, not only in the reaction crude state but especially after the diester had undergone an evaporation treatment for the purpose of removing, by distillation, excess carboxylic acid, optionally followed by a conventional decoloration treatment with activated carbon and/or hydrogen peroxide.

The Applicant has especially observed that, surprisingly and expectedly, the use of hypophosphorous acid ($H_3PO_2$) during the esterification reaction made it possible:

to obtain much less colored reaction crudes than with the use of acids that are very close structurally, such as phosphoric acid ($H_3PO_4$), most particularly recommended in Patent JP 44-2964 for sorbitan esters, or orthophosphorous acid ($H_3PO_3$);

to obtain, after purification via evaporation of said reaction crudes, compositions of which the color was identical or even less than the color before purification via evaporation, while in the absence of hypophosphorous acid or in the presence of activated carbon during the prior esterification step, the composition obtained after purification via evaporation having a significantly darker color; and to obtain, after purification via evaporation and conventional decoloration treatment, compositions with a high content of dianhydrohexitol diester(s), free from traces of organic solvents and having an absence or near absence of color never hitherto achieved.

As a result of which, the subject of the present invention is a method for preparing a composition of dianhydrohexitol diester(s), characterized in that it comprises a step during which a dianhydrohexitol composition is subjected to an esterification by a carboxylic acid in the presence of an acid catalyst and hypophosphorous acid.

The dianhydrohexitol composition used as raw material may especially be an isosorbide, isomannide, isoidide or isogalactide composition.

It may also be a mixture of these dianhydrohexitols.

This dianhydrohexitol composition may have been previously obtained by any known technique for dehydrating a hexitol or a mixture of hexitols, generally followed, after neutralization, by at least one technique for purifying the reaction crude thus obtained.

The purification step may consist of a simple distillation of the medium resulting from the dehydration. As a result of which, the dianhydrohexitol composition consists of a crude distillate, for example a crude distillate of isosorbide, isomannide and/or isoidide.

Said distillate may however have undergone at least one additional purification step, and especially:

via crystallization in an aqueous phase or in a solvent phase;

by concentration under vacuum; and/or by treatment over ion-exchange resin(s) and activated carbon, in powder and/or granular form, as described in Application WO 01/94352 in the name of the Applicant.

In any case, whether there was or was not purification after distillation, the dianhydrohexitol composition used as raw material in the method according to the invention advantageously has a content of dianhydrohexitol(s) at least equal to 95%, preferably at least equal to 98% and more preferably still at least equal to 98.5%, these percentages being expressed by total dry weight of dianhydrohexitol(s) relative to the dry weight of said composition.

The carboxylic acid used for the purpose of the esterification may especially be any acid or any mixture of acids described in any one of the aforementioned documents, in particular in the aforementioned documents U.S. Pat. Nos. 2,387,842, EP 65267, WO 99/45060 or WO 01/83488.

The carboxylic acid used, alone or as a mixture, may advantageously be a $C_2$ to $C_{24}$ acid. It may be, for example, acetic acid, n-octonoic acid, 2-ethylhexanoic acid or a mixture containing at least one of these acids.

The acid catalyst used for the purpose of the esterification may, as already emphasized, be of a very varied nature and consists not only of a macroporous resin, but also of another acid catalyst chosen, in particular, from the group formed by non-macroporous resins, hydrochloric acid, sulfuric acid, para-toluenesulfonic acid (PTSA), methanesulfonic acid, trifluoromethanesulfonic acid, trifluoroacetic acid, trichloroacetic acid, tin 2-ethylhexanoate, phosphotungstic acid and silicotungstic acid. It may be a mixture of at least two of the aforementioned acid catalysts.

The Applicant company has observed that said acid catalyst may advantageously consist of PTSA, of methanesulfonic acid, or of phosphotungstic acid.

When the acid catalyst is a resin, whether macroporous or not, it may be introduced in a lower amount to the amount described in the examples of the aforementioned Patent Application WO 01/83488, i.e. in an amount of less than about 13.7%, expressed by dry weight relative to the dry weight of dianhydrohexitol(s) used. This amount may especially be at most equal to 12% and especially be between 5 and 10%.

When the acid catalyst is not a resin, whether macroporous or not, it may advantageously be introduced in an amount between 0.05 and 5%, preferably between 0.2 and 4% by dry weight relative to the dry weight of dianhydrohexitol(s).

This amount may especially be between 0.3 and 3%, including when said catalyst is PTSA, methanesulfonic acid or phosphotungstic acid.

The general conditions for the esterification (especially the dianhydrohexitol(s)/carboxylic acid(s) molar ratio, the reaction temperature and the reaction time, and the means for removing water) are those conventionally used in the literature for the desired preparation of compositions having a high level of dianhydrohexitol diester(s).

As emphasized previously, one main feature of the present invention is to make provision, during the esterification reaction, for the presence of hypophosphorous acid ($H_3PO_2$).

This may be introduced into the reaction medium at the same time or not as the acid catalyst and/or the carboxylic acid.

According to one variant, this introduction is carried out before the start of the esterification reaction, i.e. before the introduction of the acid catalyst and/or the carboxylic acid.

According to one preferred variant, this introduction is carried out from the start of the esterification reaction.

Advantageously, and regardless of the moment when it is introduced, the hypophosphorous acid is introduced in an amount between 0.05 and 2%, preferably between 0.1 and 1%, expressed by dry weight relative to the dry weight of dianhydrohexitol(s) used.

According to another preferred variant, the hypophosphorous acid is introduced, at the same time or not as the acid catalyst for esterification, in a hypophosphorous acid/acid catalyst ratio less than 1/1, said ratio being expressed by dry weight of hypophosphorous acid relative to the dry weight of the acid catalyst.

Said ratio may especially be between 0.01/1 and 0.9/1, preferably between 0.02/1 and 0.8/1.

When the catalyst is PTSA, methanesulfonic acid or phosphotungstic acid, said ratio may advantageously be between 0.05/1 and 0.4/1.

After esterification, the reaction crude is preferably subjected, directly or indirectly, to at least one purification step.

This advantageously consists of at least one evaporation step making it possible to remove, by distillation, most or almost all, or even all, of the carboxylic acid possibly still present in this reaction crude.

During this step, the composition of dianhydrohexitol diester(s) is subjected, within the reactor or the evaporator, to high temperature conditions, between 100° C. and 250° C., and reduced pressure conditions, between 0.001 mbar and 50 mbar, conditions which strongly color the dianhydrohexitol diester compositions prepared in the absence of hypophosphorous acid.

Preferably, this step is carried out in a continuously operating evaporator.

Such a device, for example of the "falling film" type or better of the "scraped film" or "short path" type, makes it possible to limit the residence times and temperatures to which the reaction crudes are thus subjected.

As a result of which, the present invention relates to a process as described previously and characterized, moreover, in that it comprises a subsequent step of evaporation of the medium derived, directly or indirectly from the esterification step, said step being preferably carried out in a continuously operating evaporator.

Thus, a means is available that makes it possible to effectively prepare a composition of diester(s) of dianhydrohexitol(s) having a high content of diester(s), namely at least equal to 95%, preferably at least equal to 98%, this content being expressed by total dry weight of diester(s) of dianhydrohexitol(s) relative to the dry weight of said composition.

This content, for example of isosorbide di(n-octanoate) (sole diester obtained), of isoidide di(n-octanoate) (sole diester obtained) or of isosorbide di(n-octanoate)+isoidide di(n-octanoate) (obtained as a mixture) is advantageously at least equal to 98.5%.

It may be evaluated by any method available to a person skilled in the art and especially by gas chromatography, for example on a polydimethylsiloxane capillary column (DB1) with use of a flame-ionization detector (FID). The sample is injected in the form of a pertrimethylsilylated derivative (bis (trimethyl-silyl)trifluoroacetamide (BSTFA)/trimethylchlorosilane (TMCS)/pyridine). The chromatography conditions must make it possible to separate the carboxylic acid compounds, for example octanoic acid or ethylhexanoic acid optionally still present and also the tetraesters of monoanhydrohexitols optionally present.

The diesters of dianhydrohexitols are picked up by their relative retention times with respect to methyl-α-0-glucopyranoside.

Quantification of these diesters is carried out by the method of internal standardization.

The method that is the subject of the invention makes it possible to effectively obtain compositions having both high contents of diester(s) and very low coloration indices which, for some of them, have never yet been achieved hitherto.

The use, according to the invention, of hypophosphorous acid during the esterification step makes it possible, in particular, to obtain compositions of dianhydrohexitol diester(s) having yellow index (YI) values considerably lower than those obtained in the absence of this particular acid.

The yellow index (YI) value is measured here in accordance with standard ASTM D 1925-70, in particular by using the ColorFlex™ colorimeter and its usage guide as supplied by Hunterlab.

The "source" or "illuminant" consists of the "CIE Source C" or "CIE Illuminant C".

The observer consists of the "1931 CIE 2" standard observer".

The Applicant company has observed that the method according to the invention made it possible to obtain, after evaporation and before any optional additional step for purification and/or decoloration, a composition of diester(s) having a yellow index YI at most equal to 50.

Quite remarkably, this index may even be at most equal to 45, or even at most equal to 40.

It should be recalled, as already emphasized, that the evaporation step has of course the effect of (very) significantly increasing the content of dianhydrohexitol diester(s) of the composition relative to the starting reaction crude but also generally has the concomitant undesirable effect, as has been verified on numerous occasions by the Applicant, of very significantly increasing the coloration of the resulting product.

This being so, in particular, when the esterification step is carried out either in the absence of hypophosphorous acid, or in the sole presence of activated carbon as described in Example 5 of the aforementioned Patent Application WO 01/83488.

It has been observed, particularly surprisingly, that the use of hypophosphorous acid during this esterification step made it possible to obtain, directly after evaporation, diester compositions having an identical, or even lower, color than that of the reaction crudes not subjected to evaporation. This color may especially be characterized, as indicated above, by a yellow index YI at most equal to 50, a value always exceeded for a composition, after evaporation, obtained from an esterification step carried out in the absence of hypophosphorous acid and optionally in the presence of activated carbon.

The Applicant company furthermore considers, as a novel and inventive product, a composition of dianhydrohexitol diester(s), capable in particular of being obtained by the method according to the invention, characterized in that it consists of a product resulting from the esterification of a dianhydrohexitol and a carboxylic acid, then an evaporation, and in that it has a content of diester(s) at least equal to 95% and a yellow index YI at most equal to 50, preferably at most equal to 45.

Advantageously, this content of dianhydrohexitol diester(s) may be at least equal to 98% and/or this YI index may be at most equal to 40, especially at most equal to 35.

These values are all the more remarkable as they cannot be obtained for compositions of the same type obtained conventionally and treated subsequently, under conventional conditions, with activated carbon or hydrogen peroxide.

This in no way excludes furthermore that after the steps of esterification then purification, especially by evaporation, the process conforming to the invention may comprise at least one step of treating the resulting composition with activated carbon or hydrogen peroxide.

The treatment with activated carbon is carried out for example by bringing the composition into contact with 1-3% by weight of activated carbon (powdered carbon black) at a temperature close to 100° C., then by stirring at this temperature for several tens of minutes, for example for around one hour. At the end of the treatment, the activated carbon is separated by filtration.

A conventional treatment for decoloration with hydrogen peroxide consists, for example, in introducing into the composition to be decolorized, over a period ranging for example from 30 to 60 minutes, from 0.5 to 2% of 100% hydrogen peroxide at a temperature between 90° C. and 100° C., then stirring the composition for one to two hours at this temperature.

When it is desired to combine these two types of decolorizing treatment, the treatment with hydrogen peroxide preferably precedes that with activated carbon. This is because the latter makes it possible to destroy any peroxides present.

It has been observed that the use of hypophosphorous acid during the esterification step according to the invention made it possible to obtain, after evaporation then simple treatment with activated carbon under the conditions indicated above, a composition of dianhydrohexitol diester(s) having a yellow index YI at most equal to 25, or even at most equal to 20. This is all the more remarkable as according to the numerous studies and analyses carried out by the Applicant, such low values could only be obtained, in the absence of use of hypophosphorous acid, with a treatment combining activated carbon with either hydrogen peroxide or with a significant amount of n-hexane.

The subject of the present invention is therefore a composition of dianhydrohexitol diester(s) not treated with hydrogen peroxide or n-hexane, capable in particular of being obtained by the method according to the invention, characterized in that it has a yellow index YI at most equal to 25, in particular at most equal to 20.

Said composition thus characterized may advantageously have a content of diester(s) at least equal to 95%, preferably at least equal to 98%.

It has also been observed that the use of hypophosphorous acid during the esterification step made it possible, in particular, to obtain after evaporation and simple treatment with hydrogen peroxide under the conditions indicated above, a composition of dianhydrohexitol diester(s) having a yellow index YI at most equal to 15, or even at most equal to 10.

The Applicant considers that such a composition has never been obtained in the prior art or would never have been able to be obtained except, perhaps, in imagining using amounts of hydrogen peroxide greatly superior to those which may be considered as "conventional", i.e. amounts greatly superior to 1-2%.

Another subject of the present invention is a composition of dianhydrohexitol diester(s) treated with hydrogen peroxide, capable in particular of being obtained by the method according to the invention, and characterized in that it has a yellow index YI at most equal to 15, in particular at most equal to 10. This index may even be at most equal to 7.

Said composition, thus characterized, preferably has a content of diester(s) at least equal to 95%, preferably at least equal to 98%.

According to another variant, provision is moreover made that after the steps of esterification then purification, especially via evaporation, the method according to the invention comprises, in any order, at least one step of treatment with activated carbon and at least one step of treatment with hydrogen peroxide.

According to one preferred embodiment, the step of treatment with activated carbon is carried out before the step of treatment with hydrogen peroxide.

Quite remarkably, it has been observed that the use of hypophosphorous acid during the esterification step according to the invention made it possible, in particular, to obtain after evaporation then treatment with activated carbon and/or hydrogen peroxide, a composition of dianhydrohexitol diester(s) having a yellow index YI at most equal to 9, or even at most equal to 7.

This result is all the more surprising as the numerous studies and analyses carried out by the Applicant have demonstrated that such low yellow index values have never been obtained in the prior art, including according to Example 5 from the aforementioned Patent Application WO 01/83488 carried out furthermore in the presence of n-hexane, and would never have been able to be obtained in any way and this, even by imagining combining together treatment with activated carbon (including from the esterification step as provided in the aforementioned Example 5) and treatment with hydrogen peroxide, under conditions that a person skilled in the art would have judged to be reasonable.

Consequently, another subject of the present invention is a composition of dianhydrohexitol diester(s), capable of being obtained by the method according to the invention, characterized in that it has a yellow index YI at most equal to 9, in particular at most equal to 7. This value may moreover be at most equal to 6, or even at most equal to 5.

Said composition, thus characterized, may advantageously have a content of diester(s) at least equal to 95%, preferably at least equal to 98%.

Said composition is moreover preferably characterized by the fact that it is free from traces of n-hexane.

As a result of which, a particularly simple, economic, high-performance and danger-free industrial means is henceforth available, for preparing compositions having high contents of dianhydrohexitol diester(s) and which are less colored than those of the prior art.

The compositions according to the invention or obtained after purification, especially via evaporation, according to any one of the variants of the method according to the invention also have a content of diester(s) at least equal to 95%, preferably at least equal to 98%.

According to another variant, these compositions are free from traces of xylene, diethyl ether and n-hexane, i.e. traces of organic solvents used in the examples from the aforementioned international Applications WO 99/45060 and WO 01/83488.

These compositions may be used, amongst other things, in any one of the applications described or envisaged in the aforementioned documents of the prior art.

They may especially be used as additives, in particular as plasticizers, solvents, lubricants or surfactants, in the preparation of plastic compositions, bituminous or resin compositions, cellulosic compositions, compositions intended for the chemical, pharmaceutical, cosmetology, or human or animal food industries.

The compositions according to the invention may consist, amongst other things, of novel compositions of:
  isosorbide, isomannide and/or isoidide diacetate;
  isosorbide, isomannide and/or isoidide di(n-octanoate); and
  isosorbide, isomannide and/or isoidide di(2-ethylhexanoate).

Regarding the specific preparation of isoidide diesters, a preparation which has never been exemplified hitherto, it has been observed moreover that the method according to the invention made it possible to obtain such products under conditions even more favorable than in the case of isosorbide diesters, and especially:
  for significantly shorter esterification reaction times, for example of 3.5 hours instead of 5 hours; and
  resulting in products, for example evaporated reaction crudes, optionally treated with activated carbon, having further improved color.

The Applicant company furthermore considers that a composition having a content of isoidide diester(s) at least equal to 95%, capable in particular of being obtained by the method according to the invention, constitutes a product that is novel in itself, independently of any other characteristic.

Such a composition preferably has a yellow index YI at most equal to 50.

It may be, in particular, a composition having a content, for example of isoidide di(n-octanoate) and/or di(2-ethylhexanoate), at least equal to 98% and a yellow index YI at most equal to 25.

Such a composition may also be characterized in that it is free from traces of xylene, diethyl ether and n-hexane.

Such compositions are shown to be plasticizer compositions for plastic or bituminous materials that are as high performance, or even more high performance for certain aspects, than the corresponding compositions based on isosorbide diester(s).

Considering all the preceding, the Applicant company furthermore considers that one subject of the present invention consists overall of the use of hypophosphorous acid during the esterification of a dianhydrohexitol in the presence of an acid catalyst.

The present invention will be described in even greater detail using the examples which follow and which are in no way limiting.

EXAMPLE 1

A test according to the invention (TEST 1) was carried out according to the following general procedure.

Introduced into a 1-liter glass reactor equipped with a jacket fed by a thermostated bath having a circulation of oil, a propeller-type stirrer blade, a thermometer, a distillation head combined with a condenser and a distillation collector, were 146 g of isosorbide (1 mol) and 432 g of n-octanoic acid (3 mol).

The stirrer system was operated at 400 rpm, and the thermostated bath with a setting of 100° C. When the temperature of the reaction medium reached 60° C., the following were added: 2.92 g of p-toluenesulfonic acid (PTSA) monohydrate (which corresponded to 1.8% by dry weight relative to the dry isosorbide) and 0.90 g of 50% hypophosphorous acid, namely 0.3% by weight of dry matter relative to the dry isosorbide and in a ratio of around 0.15/1 relative to the PTSA.

The setting of the thermostated bath was then fixed at 150° C. and the stirring at 650 rpm. The whole of the assembly was then connected to a vacuum pump equipped with a vacuum meter, of which the setting was fixed at 100 mbar.

When the temperature of the reaction medium reached around 115° C., the water from the esterification reaction was distilled and recovered in the collector. After 2 hours of reaction, the amount of water distilled corresponded to around 85% of the theoretical amount of water for a complete reaction. The vacuum was then gradually reduced over 3 additional hours to 25 mbar, while the temperature of the reaction medium naturally reached 140° C. After 5 hours of reaction, the distilled water reached 97% of the theoretical value.

The reaction medium was then cooled to around 100° C., and the strong acidities of the PTSA and of the hypophosphorous acid were neutralized by addition of 1.8 g of 50% sodium hydroxide. After precipitation of the salts formed, the reaction medium was filtered and was then in the form of a clear yellow liquid. The yellow index YI of this neutralized/filtered reaction crude, measured as described previously, gave a value of 50.7.

After returning to the reactor, the octanoic acid which had not reacted was distilled under vacuum (5 mbar; vapor temperature: 115° C.). The temperature of the reboiler changed from 130 to around 200° C. during this evaporation. The thus purified composition had a content of isosorbide di(n-octanoate) of 98.5%.

This content was measured by gas chromatography on a Varian 3400 type machine with FID detection and a type 1077 split/splitless injector. The column used was a DB1 of brand J & W Scientific having a length of 30 meters, an internal diameter of 0.32 mm and a film thickness of 0.25 μm. The temperature conditions were: injector and detector: 300° C.; column: programmed from 100° C. to 320° C. at a rate of 7° C./min, hold for 10 min at 320° C. The injection was carried out as a split injection at 80 ml/min, the pressure at the top of the column being 14 psi and the carrier gas used being helium.

The content is given, after internal standardization, by the sum of the relative proportions of the areas of the compounds of which the relative retention time is between 1.52 and 1.72.

Moreover, and remarkably, the color of the composition having undergone an evaporation was not degraded relative to that of the neutralized/filtered reaction crude obtained before evaporation. Specifically, said composition obtained therefore according to the invention had a YI index of 49.8.

Within the context of a control test carried out in the absence of any use of hypophosphorous acid during the esterification reaction (TEST C1), obtained under the same general conditions were:
- not only a neutralized/filtered reaction crude of brown color (YI index of 106.1);
- but also, after evaporation, a composition having an even darker color (YI index of 149.4).

This composition moreover had a content of isosorbide di(n-octanoate) of less than 98.5%.

EXAMPLE 2

Other tests (hereinafter TESTS 2 to 7), also according to the invention, were carried out according to the general procedure described for TEST 1, apart from the fact that the following modifications were introduced:
- TEST 2: the esterification reaction was carried out for a duration of 6 hours instead of 5 hours;
- TEST 3: the 1.8% by dry weight of PTSA was replaced with 1.1% of methanesulfonic acid;
- TEST 4: the 1.8% by dry weight of PTSA were replaced with 11% of macroporous resin of "Amberlyst 15 (Dry)" type;
- TEST 5: the 1.8% by dry weight of PTSA were replaced with 1.9% by dry weight of phosphotungstic acid, the esterification reaction being carried out under nitrogen sparging and not under vacuum;
- TEST 6: the n-octanoic acid was replaced (mol/mol) with 2-ethylhexanoic acid, the esterification reaction being furthermore carried out for a duration of 7.5 hours, at a temperature of 160-175° C. and under a vacuum of 100 mbar; and
- TEST 7: the isosorbide was replaced with isoidide, the esterification reaction having been able to be carried out furthermore in 3.5 hours instead of 5 hours.

The table below shows, for each of the TESTS 2 to 7 according to the invention (use of $H_3PO_2$ during the esterification), the yellow index obtained for the neutralized/filtered reaction crude (hereinafter "YI REAC"), the yellow index obtained subsequently after evaporation (hereinafter "YI EVAP") and the diester content obtained for the composition resulting from the evaporation (hereinafter "% CONT"), being understood that this content relates to:
- isosorbide di(n-octanoate) for TESTS 2 to 5;
- isoidide di(n-octanoate) for TEST 7, said content being measured as described previously for isosorbide di(n-octanoate); and
- isosorbide di(2-ethylhexanoate) for TEST 6, said content being measured as described previously apart from the fact that, after internal standardization, taken into account was the sum of the relative proportions of the areas of the compounds of which the relative retention time was, this time, between 1.44 and 1.55.

| TEST | YI REAC | YI EVAP | % CONT |
|------|---------|---------|--------|
| 2 | 50.0 | 32.5 | 98 |
| 3 | 75.0 | 42.3 | 99 |
| 4 | 56.6 | 38.7 | 95 |
| 5 | 33.9 | 25.4 | 97 |
| 6 | 26.5 | 17.6 | 99 |
| 7 | 71.5 | 40.6 | 99 |

These TESTS 2 to 7 confirm that the compositions according to the invention may simultaneously have, after evaporation of the reaction crude:

not only a high content of dianhydrohexitol diester(s);

but also a non-degraded, generally improved, color relative to that of the reaction crude.

Remarkably, this color may be characterized by a yellow index YI not only at most equal to 50 but also at most equal to 45, or even 40 or even still 35.

These TESTS 2 to 7 furthermore show that within the scope of the invention, it is possible to advantageously replace a macroporous resin by a whole range of other acid catalysts such as PTSA, methanesulfonic acid or phosphotungstic acid.

Solely in terms of content, these acid catalysts are proved here to be higher performing than the macroporous resin which, in the present case, makes it possible however to achieve a diester content of 95%.

The Applicant company has furthermore observed, during in-depth analyses, that in the particular case of a macroporous resin as a catalyst, the majority of the impurities present consisted of esters, in particular tetraesters, of sorbitan, which implies that in the presence of this type of catalyst, the dianhydrohexitol undergoes a degradation by ring-opening during the esterification.

As already emphasized, the method according to the invention also has the unsuspected advantage of allowing the effective preparation of novel compositions not only of isosorbide diester(s), for example isosorbide di(n-octanoate) and also isosorbide di(2-ethylhexanoate), but also of isoidide diester(s), for example isoidide di(n-octanoate).

Dramatically, it is observed that the use of hypophosphorous acid during the esterification step of the isoidide, which step may furthermore take place in remarkably short reaction times (<4 hours), generates a reaction crude of which the color (YI index of 71.5) may then be reduced by more than 30 units (YI index of 40.6) during the purification step via evaporation.

EXAMPLE 3

Within the context of this example, tests that did not conform to the invention (TESTS C2 to C5) were carried out in the same way as for TEST C1 according to Example 1, apart from the fact that the following modifications were introduced:

TEST C2: same as TEST C1 except that the esterification (in the absence therefore of hypophosphorous acid) was carried out in the presence a) of "Amberlyst 15 (dry)" resin (by replacing PTSA) and also b) activated carbon, according to Example 5 of the aforementioned Application WO 01/83488;

TEST C3: same as TEST C2 except that after evaporation of the reaction crude and concomitant distillation of the excess n-octanoic acid, the resulting composition was subjected to an additional treatment of decoloration with activated carbon;

TEST C4: same as TEST C3 except that after evaporation of the reaction crude, the resulting composition was subjected to an additional treatment with solvent (n-hexane) and activated carbon, according to Example 5 of Patent WO 01/83488; and TEST C5: same as TEST C1 except that the hypophosphorous acid ($H_3PO_2$) was replaced (weight/weight) with phosphoric acid ($H_3PO_4$).

The table below shows, for each of the TESTS C2 to C5, which did not conform to the invention (absence of $H_3PO_2$ during the esterification), the values obtained for the predefined criteria "YI REAC", "YI EVAP" and "% CONT".

| TEST | YI REAC | YI EVAP | % CONT |
|------|---------|---------|--------|
| C2 | 22.5 | 52.7 | 94 |
| C3 | 22.5 | 30.9 | 94 |
| C4 | 22.5 | 28.2 | 94 |
| C5 | 132.0 | 180.1 | 97 |

The results of TESTS C2 to C4 show that although the presence of activated carbon during the esterification reaction makes it possible to obtain a reaction crude with acceptable color (YI index of 22.5), the fact still remains that:

after evaporation (TEST C2), this color degrades very significantly (YI index increased by around 30 units) to reach a value >50 (52.7);

a subsequent treatment with activated carbon does not make it possible to obtain a YI index at most equal to 30 (YI of 30.9); and a subsequent treatment with n-hexane and activated carbon does not make it possible to obtain a YI index at most equal to 25 (YI of 28.2).

For these TESTS C2 to C4, the content of isosorbide di(n-octanoate) is less than 95% due to the presence of significant amounts of sorbitan tetraesters, apparently linked to the use of a macroporous resin as acid catalyst for esterification.

The results of TEST C5 furthermore show that it is not possible to replace hypophosphorous acid with phosphoric acid.

The latter not only makes it impossible to obtain a reaction crude of which the YI index is at most equal to 50, the value found (132.0) being very significantly higher than this limit, but also this high value of the YI index is very strongly increased by the evaporation step.

Moreover, the content of isosorbide di(n-octanoate) obtained after evaporation for this TEST C5 was only 97%.

EXAMPLE 4

Tests conforming to the invention (TESTS 8 to 11) were carried out according to the general procedure described for TEST 1 or TEST 2, apart from the fact that after the step of distilling octanoic acid, the resulting diester composition, purified by evaporation, was subjected respectively to each of the following treatments:

TEST 8: TEST 1+treatment with 2% by (dry/dry) weight of activated carbon;

TEST 9: TEST 1+treatment with 1% by weight of 100% hydrogen peroxide;

TEST 10: TEST 2+treatment with 1% by weight of 100% hydrogen peroxide; and

TEST 11: same as TEST 10+subsequent treatment with 2% by (dry/dry) weight of activated carbon.

All of the compositions conforming to the invention thus prepared according to Examples 8 to 11 have shown a high content of isosorbide di(n-octanoate), of around 99%.

The table below shows, for each of said TESTS, the yellow index YI value obtained for the resulting diester composition.

|    | TEST 8 | TEST 9 | TEST 10 | TEST 11 |
|----|--------|--------|---------|---------|
| YI | 18.7   | 6.8    | 9.3     | 5.0     |

It is quite remarkable to observe that, due to the method according to the invention, it is possible to obtain compositions of dianhydrohexitol diester(s) which have not undergone any treatment with an organic solvent, having:

a yellow index at most equal to 25, or even 20, in the absence of any treatment with hydrogen peroxide (cf. TEST 8); or a yellow index at most equal to 15, or even 10 (cf. TEST 10), or even still 7 (cf. TEST 9) via a simple treatment with hydrogen peroxide, in the absence of any treatment with activated carbon; or a yellow index at most equal to 9, or even 7, or even still 6 or 5, via treatment with "reasonable" amounts of hydrogen peroxide then activated carbon (cf. TEST 11).

These results are all the more surprising as the control tests, carried out according to TEST C1 (absence of hypophosphorous acid during the esterification) but envisaging, after the evaporation step, treatments with either 2% of 100% hydrogen peroxide, or 1% of hydrogen peroxide then 2% of activated carbon, have not made it possible to prepare compositions of isosorbide di(n-octanoate) having a yellow index YI at most equal to 20.

The invention claimed is:

1. A composition of dianhydrohexitol diester(s), comprising a reaction product resulting from esterification of a dianhydrohexitol with a carboxylic acid in the presence of an acid catalyst and hypophosphorous acid, and then evaporation,
wherein the composition has a diester content of at least 95 wt % and a yellow index (YI) of less than or equal to 50, according to an ASTM D 1925-70 standard.

2. The composition according to claim 1, wherein the composition has a diester content of at least 98 wt %.

3. The composition according to claim 1, wherein the composition has a YI of less than or equal to 40.

4. The composition according to claim 1, wherein the composition has a YI of less than or equal to 25.

5. The composition according to claim 1, wherein the composition has a YI of less than or equal to 20.

6. The composition according to claim 1, wherein the composition has a YI of less than or equal to 15.

7. The composition according to claim 1, wherein the composition has a YI of less than or equal to 10.

8. The composition according to claim 1, wherein the composition has a YI of less than or equal to 7.

9. The composition according to claim 1, wherein the reaction product is further decolored by treating with at least one of activated carbon, hydrogen peroxide, n-hexane, or any combination thereof.

10. The composition according to claim 9, wherein the reaction product is further decolored by treating with hydrogen peroxide and the composition has a YI of less than or equal to 10.

11. The composition according to claim 1, wherein the reaction product is not further decolored by treating with at least one of activated carbon, hydrogen peroxide, n-hexane, or any combination thereof, and the composition has a YI of less than or equal to 20.

12. The composition according to claim 1, wherein the composition is free from traces of xylene, diethyl ether and n-hexane.

13. The composition according to claim 1, wherein the dianhydrohexitol comprises an isosorbibe, isomannide, isoidide, isogalactide or any combination thereof.

14. The composition according to claim 1, wherein the carboxylic acid comprises acetic acid, n-octonoic acid, 2-ethylhexanoic acid, or any combination thereof.

15. The composition according to claim 1, wherein the acid catalyst comprises hydrochloric acid, sulfuric acid, para-toluenesulfonic acid, methanesulfonic acid, trifluoromethanesulfonic acid, trifluoroacetic acid, trichloroacetic acid, tin 2-ethylhexanoate, phosphotungstic acid, silicotungstic acid, or any combination thereof.

16. The composition according to claim 1, wherein the acid catalyst comprises a resin.

17. The composition according to claim 1, wherein the dianhydrohexitol diester(s) comprise isosorbide, isomannide, isoidide diacetate, isoidide di(n-octanoate), isoidide di(2-ethylhexanoate), or any combination thereof.

* * * * *